United States Patent [19]

Yoshida

[11] Patent Number: Plant 7,743

[45] Date of Patent: Dec. 10, 1991

[54] AFRICAN VIOLET NAMED 'MARLA'

[76] Inventor: Eiichi Yoshida, P.O. Box 4836, Hayward, Calif. 94540-4836

[21] Appl. No.: 524,125

[22] Filed: May 14, 1990

[51] Int. Cl.[5] ..... A01H 5/00

[52] U.S. Cl. ..... Plt./69

[58] Field of Search ..... Plt./69

*Primary Examiner*—James R. Feyrer

[57] ABSTRACT

A new variety of African violet plant for potted plant culture particularly distinguished by its year 'round blooming capability, its profuse production of semi-double, ruffle edged flowers, and its compact growth with abundant foliage of solid green color which provides a spreading base and attractive backing for the clusters of blossoms.

1 Drawing Sheet

BACKGROUND OF THE NEW PLANT

This new and distinct cultivar of African violet, botanically known as *Saintpaulia ionantha* and hereinafter referred to by the cultivar name Marla. Marla was obtained by cross-pollenating the seed parent "Melodie" Rhonda and the pollen parent "Melodie" Farrah×'-'Sylvan Blue". The seed pods of the pollenated plants were used as the generic basis for initiating further propagation trials. Seeds of the stated cross were planted in the hopes of obtaining offspring plants which retained one or more of the most desireable characteristics of each of the plants in the indicated lineage. From an initial twelve seedling selections which were retained for evaluation and testing to determine the characteristics and attributes of each selected individual from the noted cross, one outstanding individual occured, which is the selected plant of this specification.

The plant of this disclosure was selected based on a number of outstanding characteristics which were not seen as combine characteristics in previous plants of this market class. Among these are an uncommonly low, attractive rosette growth habit with large, attractive leaves of uniform, flat shaped and slight crenate margins rendering specimens of low but strong appearance and of excellent exhibition form. The plant, subsequently denominated 'Marla', further displays prolific production of large, weighty pink blossoms which have five primary petals which are ruffled at the outer portions, and which have an ununiform number of secondary petals or petaloids which effect an unusually expansive color splash of semi-double flowers appearing just above the foliage.

I have asexually reproduced 'Marla' by taking leaf cuttings to start plants in the manner traditional in multiplying *Saintpaulia ionantha* specimens resulting from such asexual reproduction have been observed to be identical to the parent in all distinguishing characteristics to establish that 'Marla' is a genetically stable plant.

BRIEF DESCRIPTION OF THE DRAWING

Sheet one is a full color photographic view of the plant in bloom, the colors shown being as nearly true as it is reasonably possible to obtain by conventional photographic procedures.

The following is a detailed description of my new African violet plant with the color designation being accorded to the R.H.S. Colour Chart published by The Royal Horticultural Society of London, England, with collaboration by The British Colour Council.

THE PLANT

Name: Marla.

Origin: Seedling.

Parentage:

*Seed parent.*—Saintpaulia "Melodie" Rhonda.

*Pollen parent.*—Saintpaulia "Melodie" Farrah×-Saintpaulia "Sylvan Blue".

Classification:

*Botanic.*—*Saintpaulia ionantha.*

*Commercial.*—African violet.

Form: Rosette arrangement.

Height: 7 to 9 cm.

Growth: Moderate, petioles at first upright, becoming horizontal with age.

Size: Medium, to 21 cm. in diameter.

Mutation prone: Flowers occasionally produce extra stamens.

Foliage:

*Shape.*—Ovate, slight cordate base, rounded tip, slight crenate margin.

*Length.*—7 to 8 cm. on mature leaves.

*Width.*—6 to 7 cm. on mature leaves.

*Color.*—Upperside: Dark green. Underside: Red, darker towards midvein.

*Texture.*—Upperside: Pubescent. Underside: Puberulent.

*Ribs and veins.*—Pronounced, pinnate, red pigmented.

*Petiole.*—Flattened above, pubescent, red pigmented.

THE FLOWER

Blooming habit: Continuous and abundant under optimal growing conditions. Profuse flowering.

Number: 7 to 9 per peduncle.

Size of flower: Each flower is approximately 4 to 5 cm.

Color: Red-Purple, R.H.S. 69A.

Type: Semi-double, violet-like.

Petals: Five main petals with several smaller petals clustered around the reproductive organs, margins ruffled.

Texture: Smooth, slightly flexible.

Appearance: Upperside glabrous, lowerside slightly puberulent.

Peduncles: 5 to 6 cm. in height, pubescent, red pigmented.

Inflorescence: Cyme, upright, above the foliage.

Calyx: Quinquepartite, red pigmented, puberulent.

Persistence: Flowers do not drop, long lasting. After maturity the flowers dry off and remain on the peduncle without becoming infected by botrytis.

Fragrance: None.

REPRODUCTIVE ORGANS

Stamens: Usually two per flower.

*Anthers.*—Bright yellow, basifixed, two per filament.

*Filaments.*—c. 0.3 cm. in length.

*Pollen.*—Light yellow.

Pistils: Normally one per flower.

*Stigma.*—Visible and accessible, becoming swollen when receptive and exuding a droplet of clear liquid.

*Style.*—c. 0.7 cm. in length.

*Ovary.*—Superior.

I claim:

1. A new and distinct cultivar of African violet named 'Marla', as described and illustrated, and particularly characterized by its delicate pink color, profuse flowering, upright flower stems, compact bouquet, vigorous growth habit, flowering 11 to 12 weeks after potting and its long lasting and non-dropping flowers.

* * * * *

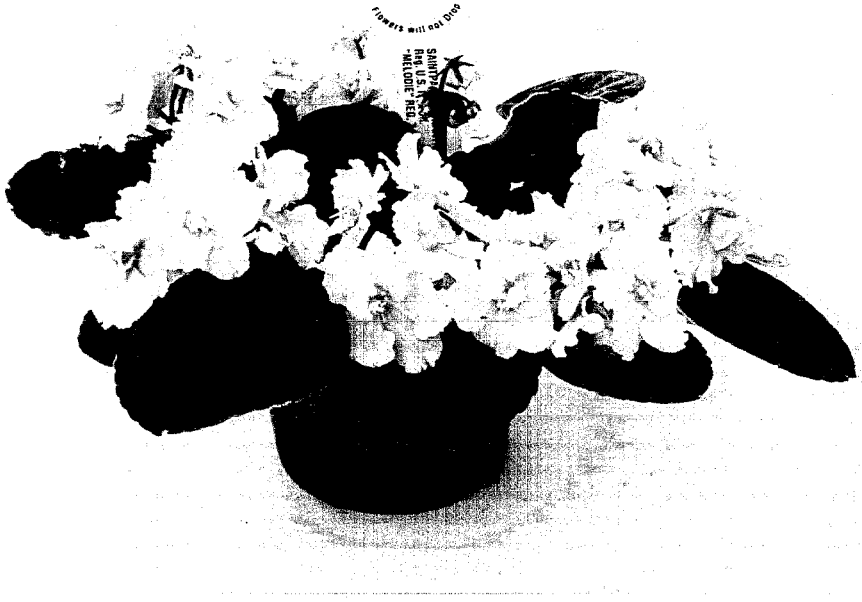
Flowers will not Drop
SANTA
Reg U.S.
"MELODIE"